United States Patent
Sohn et al.

(10) Patent No.: US 10,427,148 B2
(45) Date of Patent: Oct. 1, 2019

(54) DETERGENT ALKYLATION CATALYST REGENERATION EFFLUENT RECYCLE

(71) Applicant: UOP LLC, Des Plaines, IL (US)

(72) Inventors: Stephen W. Sohn, Arlington Heights, IL (US); Charles P. Luebke, Mount Prospect, IL (US); Jeffrey L. Pieper, Des Plaines, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 16/058,841

(22) Filed: Aug. 8, 2018

(65) Prior Publication Data
US 2018/0345268 A1 Dec. 6, 2018

Related U.S. Application Data

(63) Continuation of application No. PCT/US2017/030963, filed on May 4, 2017.

(60) Provisional application No. 62/338,891, filed on May 19, 2016.

(51) Int. Cl.
| | |
|---|---|
| *B01J 38/48* | (2006.01) |
| *C07C 2/66* | (2006.01) |
| *B01J 38/04* | (2006.01) |
| *B01J 21/20* | (2006.01) |
| *B01J 27/32* | (2006.01) |
| *B01J 29/90* | (2006.01) |
| *B01J 19/24* | (2006.01) |
| *C07C 6/06* | (2006.01) |

(52) U.S. Cl.
CPC ............... *B01J 38/48* (2013.01); *B01J 19/24* (2013.01); *B01J 21/20* (2013.01); *B01J 27/32* (2013.01); *B01J 29/90* (2013.01); *B01J 38/04* (2013.01); *C07C 2/66* (2013.01); *C07C 6/06* (2013.01); *B01J 2219/00222* (2013.01); *B01J 2219/24* (2013.01); *Y02P 20/584* (2015.11)

(58) Field of Classification Search
CPC ... B01J 38/48; B01J 19/24; B01J 21/20; B01J 38/04; B01J 29/90; B01J 27/32; B01J 2219/00222; B01J 2219/24; C07C 6/06; C07C 2/66; Y02P 20/584
See application file for complete search history.

(56) References Cited

U.S. PATENT DOCUMENTS

| | | | |
|---|---|---|---|
| 2008/0194895 A1* | 8/2008 | Sohn | C07C 2/66 585/435 |
| 2015/0251975 A1* | 9/2015 | Jani | C07C 2/66 585/323 |

* cited by examiner

*Primary Examiner* — In Suk C Bullock
*Assistant Examiner* — Jason Y Chong

(57) ABSTRACT

A process for the regeneration of a catalyst is presented. The catalyst is in a reactor for use in benzene alkylation, and periodically needs to be regenerated. The reactor is taken off-line, and a regenerant is passed through the reactor, producing an effluent stream. A portion of the effluent stream is recycled through the reactor without passing through a clean-up process.

20 Claims, 1 Drawing Sheet

DETERGENT ALKYLATION CATALYST REGENERATION EFFLUENT RECYCLE

CROSS-REFERENCE TO RELATED APPLICATIONS

This application is a Continuation of copending International Application No. PCT/US2017/030963 filed May 4, 2017, which application claims priority from U.S. Provisional Application No. 62/338,891 filed May 19, 2016, the contents of which cited applications are hereby incorporated by reference in their entirety.

FIELD OF THE INVENTION

The present invention relates to the process of benzene alkylation. In particular, the invention relates to the regeneration of the catalyst used in benzene alkylation.

BACKGROUND

Alkylation of benzene with olefin of 8 to 16 carbon atoms produces alkylbenzenes that may find various commercial uses, e. g., alkylbenzenes can be sulfonated to produce detergents. As used herein, alkylbenzenes refers to phenyl-alkanes wherein the alkane group has between about 8 and 16 carbon atoms. Alkylbenzenes are produced as a commodity product in large-scale facilities, e. g. often in amounts of 50, 000 to 200, 000 metric tonnes per year per plant. In the alkylation process, benzene is reacted with an olefin the desired length to produce the sought alkylbenzene. The alkylation conditions comprise the presence of homogeneous or heterogeneous alkylation catalyst such as aluminum chloride, hydrogen fluoride, silica alumina or zeolitic catalysts and elevated temperature.

The alkylbenzene must meet stringent product specifications to be commercially acceptable. For instance, alkylbenzenes, to be desirable for making sulfonated surfactants, must be capable of providing a sulfonated product of suitable clarity, biodegradability and efficacy. The benzene content of the alkylbenzene product should be relatively free from benzenes, e. g. less than about 1 part per million by weight (ppmw), and often less than about 0.5 ppmw. Also, desirable alkylbenzene products are relatively free, e. g., less than about 50, preferably less than about 5, ppmw, from byproducts such as dialkylbenzenes, oligomers of olefins, and the like (herein referred to as "heavies"). Additional considerations for commercial alkylbenzene products include the 2-phenyl content and linearity of the alkyl substituent. With respect to efficacy, alkylbenzenes having higher 2-phenyl contents are desired as they tend, when sulfonated, to provide surfactants having better detergency but less solubility if the 2-phenyl content becomes too high. Thus alkylbenzenes having a 2-phenyl isomer content in the range from about 25 to about 40 percent are particularly desired.

The production of detergents involves a lot of resources, and with the demand for high quality detergents, there is a continuous need to improve the processes for producing linear alkylbenzenes.

SUMMARY

A process is presented for the regeneration of a catalyst used in the benzene alkylation process.

A first embodiment of the invention is a process for the regeneration of an alkylation reactor, comprising: taking an alkylation reactor unit off-line to create an off-line reactor; passing a regenerant stream to an inlet port of the off-line reactor to generate a regenerant effluent, during a regeneration cycle; and passing a portion of the regenerant effluent to inlet port of the off-line reactor, wherein the portion is greater than 10 vol %. An embodiment of the invention is one, any or all of prior embodiments in this paragraph up through the first embodiment in this paragraph wherein the portion is between 50 vol % and 95 vol %. An embodiment of the invention is one, any or all of prior embodiments in this paragraph up through the first embodiment in this paragraph wherein the portion is between 75 vol % and 85 vol %. An embodiment of the invention is one, any or all of prior embodiments in this paragraph up through the first embodiment in this paragraph wherein the mass flux through the off-line reactor is between 40 kg/hr/m$^2$ and 500 kg/hr/m$^2$. An embodiment of the invention is one, any or all of prior embodiments in this paragraph up through the first embodiment in this paragraph wherein the mass flux through the off-line reactor is between 250 kg/hr/m$^2$ and 400 kg/hr/m$^2$. An embodiment of the invention is one, any or all of prior embodiments in this paragraph up through the first embodiment in this paragraph wherein the off-line reactor is purged with the regenerant stream. The process of claim 6 wherein the off-line reactor is heated to a regeneration temperature. An embodiment of the invention is one, any or all of prior embodiments in this paragraph up through the first embodiment in this paragraph wherein the regeneration temperature is between 200° C. and 300° C. An embodiment of the invention is one, any or all of prior embodiments in this paragraph up through the first embodiment in this paragraph wherein the off-line reactor is cooled to a process temperature. An embodiment of the invention is one, any or all of prior embodiments in this paragraph up through the first embodiment in this paragraph wherein the off-line reactor is placed on-line. An embodiment of the invention is one, any or all of prior embodiments in this paragraph up through the first embodiment in this paragraph further comprising passing a second portion of the regenerant effluent stream to a transalkylation reaction unit. An embodiment of the invention is one, any or all of prior embodiments in this paragraph up through the first embodiment in this paragraph wherein the second portion is less than 50 vol % of the regenerant effluent stream. An embodiment of the invention is one, any or all of prior embodiments in this paragraph up through the first embodiment in this paragraph wherein the regenerant is benzene. An embodiment of the invention is one, any or all of prior embodiments in this paragraph up through the first embodiment in this paragraph wherein the regeneration cycle is between 1 and 72 hours.

A second embodiment of the invention is a process for the production of monoalkylbenzene comprising passing a feedstream comprising unbranched and lightly branched olefins to an on-stream alkylation reaction unit; passing an aromatic stream to the alkylation reaction unit to react with the olefins in the feedstream to generate an effluent stream comprising alkylbenzenes; after a process cycle, moving the on-stream alkylation reaction unit to off-stream status, and bringing an off-stream alkylation reaction unit on-stream; passing a regenerant stream to the off-stream alkylation reaction unit during a regeneration cycle, thereby generating a regenerant effluent stream, wherein the regenerant is an aromatic stream; and passing a portion of the regenerant effluent stream to the off-stream alkylation reaction unit, wherein the portion of the regenerant effluent stream is greater than 20% of the regenerant effluent stream. An embodiment of the invention is one, any or all of prior embodiments in this paragraph up through the second embodiment in this paragraph wherein the portion is between 75 vol % and 85 vol %. An embodiment of the invention is one, any or all of prior embodiments in this paragraph up through the second embodiment in this paragraph wherein the mass flux through the off-line reactor is between 250 kg/hr/m$^2$ and 400 kg/hr/m$^2$. An embodiment of the invention is one, any or all of prior embodiments in this paragraph up through the second embodiment in this paragraph wherein the feedstream comprises unbranched and lightly branched olefins having from 8 to 16 carbon atoms. An embodiment of the invention is one, any or all of prior embodiments in this paragraph up through the second embodiment in this paragraph wherein the regeneration cycle is between 1 and 72 hours. An embodiment of the invention is one, any or all of prior embodiments in this paragraph up through the second embodiment in this paragraph further comprising passing a second portion of the regenerant effluent stream to a transalkylation reaction unit.

In the foregoing, all temperatures are set forth in degrees Celsius and, all parts and percentages are by weight, unless otherwise indicated.

Other objects, advantages and applications of the present invention will become apparent to those skilled in the art from the following detailed description and drawings.

DETAILED DESCRIPTION

Various processes have been proposed for the alkylation of benzene. See, for instance, Pujado, Linear Alkylbenzene (LAB) Manufacture, HANDBOOK OF PETROLEUM REFINING PROCESSES, Second Edition, pp 1.53 to 1.66 (1996). One type of process uses a solid acidic catalyst involving contacting an olefin with a stoichiometric excess of benzene at elevated temperature to produce alkylbenzene. The reaction product stream will contain, in addition to alkylbenzene, benzene, some unreacted olefin, and reaction byproducts such as dialkylbenzene and oligomers and polymers of the olefin. For commercial processes, the feedstocks may include other components as well. For instance, the olefin may be obtained by the dehydrogenation of a paraffinic feedstock and thus contain significant amounts of paraffin.

The process of benzene alkylation utilizes a catalyst that periodically needs to be regenerated. The regeneration process involves the use of a regenerant fluid, typically an aromatics compound. The regenerant can comprise benzene, toluene, xylenes, ethylbenzene, or mixtures thereof. A preferred regenerant is benzene. In the benzene alkylation process, the process generally includes two or more reactors, with each reactor under a process cycle, a regeneration cycle, or an idle cycle. A process cycle is when the reactor is being used to actively generate a product stream. A regeneration cycle is when a reactor is undergoing regeneration to refresh the catalyst for reuse in a process cycle. An idle cycle is when a reactor has been regenerated, but has not been brought back on-line for a process cycle.

A typical regeneration cycle includes a purge stage, a temperature ramp-up stage, a temperature hold stage, and a cool down stage to the process temperature. The present invention adds a regenerant recycle step during the temperature ramp-up stage and the temperature hold stage of the regeneration process.

Improvements have involved new and improved catalysts, and energy integration methods. Improvements have also included reuse of the regenerant, when the regenerant is benzene, by passing the regenerant stream to another reactor, such as the transalkylation reactor, or even the alkylation reactor. The regeneration process requires fresh benzene, and the production of benzene is an expensive process in terms of energy. This energy burden affects the process economics for LAB production. The production of LABs utilizes unbranched and lightly branched olefins having from 8 to 16 carbon atoms. These LABs are useful for the production of detergents. Further, as used herein, "lightly-branched non-normal hydrocarbons" include isoparaffins having no more than two methyl groups and no other branches. Also, as used herein, "heavier-branched non-normal hydrocarbons" include aromatics, isoparaffins having more than two methyl groups, and isoparaffins having at least one branch longer than a methyl group.

Figure 1:
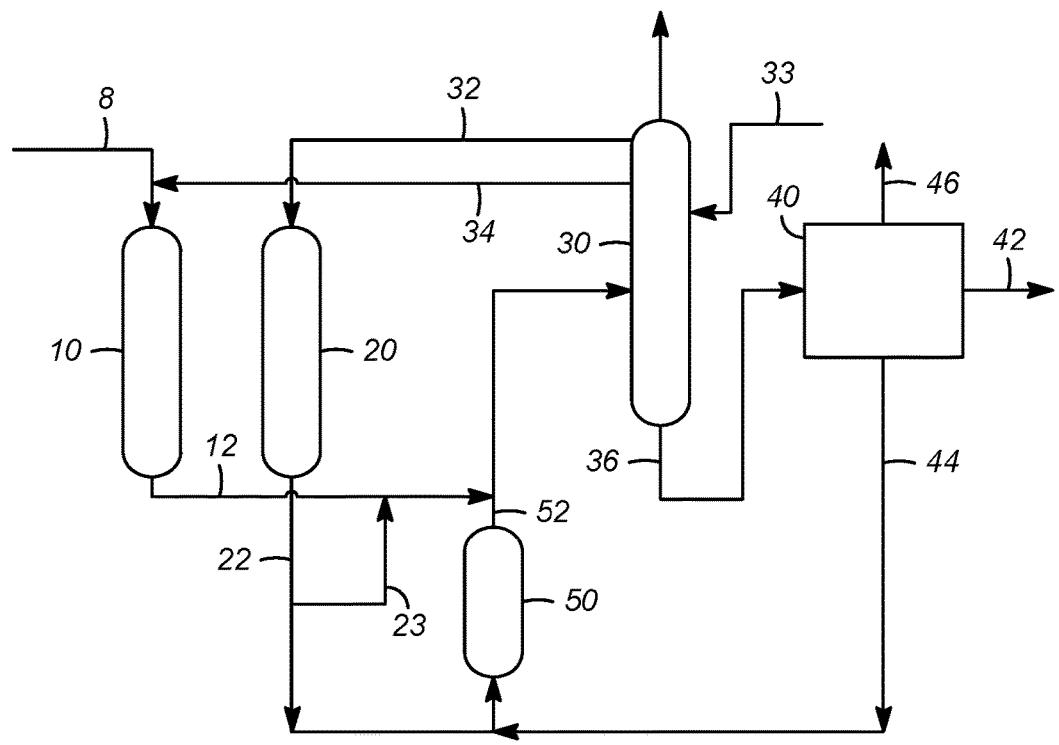
FIG. 1 is a diagram of the process for benzene alkylation to generate LABs.

The process of benzene alkylation is shown in FIG. 1, wherein an olefin stream 8 is passed to an on-line alkylation reactor 10, to generate a process stream 12 comprising alkylbenzenes, benzene and other products. The process stream 12 is passed to a benzene column 30 to separate and recover benzene for reuse. The benzene column 30 generates a regenerant stream 32, a recycle stream 34, and an alkylbenzene process stream 36. The alkylbenzene process stream 36 is passed to a product recovery unit 40 to generate an LAB product stream 42, a heavies stream 44, and other process streams 46. In the product separation process, while it is desired to remove as much of the benzene from the process stream in the benzene column, the LAB product stream can be passed through a clay treater. This allows for a higher content of benzene passed to the product recovery unit 40, where the heavies stream 44 can include benzene up to values of 2500-3000 ppm wt. The other process streams 46 can be separate streams that include recycle paraffins or light components that are passed to upstream processing units. The heavies stream 44 comprises dialkylbenzenes and trialkylbenzenes. These are byproducts that can be recycled. A fresh make-up benzene stream 33 can be added to the process, either a line to the alkylation reactor, a line to the off-line reactor, or to the benzene column 30.

The recycle stream 34 is passed to the on-line reactor 10 and provides benzene for the alkylation reaction. The regenerant stream 32 is passed to an off-line reactor 20 to regenerate the alkylation catalyst within the reactor 20, and generates a spent regenerant stream 22. The spent regenerant stream 22 is passed to a transalkylation reactor 50. When the process does not have a transalkylation reactor, the spent regenerant stream 22 is passed to the benzene column 30 via line 23. The spent regenerant contains materials deposited on the catalyst which needs to be removed from the reactor 20. The heavies stream 44 is passed to the transalkylation reactor 50 and makes use of the spent regenerant to convert the heavies to more LABs. The transalkylation reactor 50 generates an effluent stream 52 comprising benzene and LABs. The effluent stream 52 is passed to the benzene column 30 to recover product and recycle unreacted benzene.

The present invention has found that during regeneration, the regenerant can be recycled through the off-line reactor during the regeneration phase without any deleterious effects to the catalyst bed. It was found that the amount of materials removed from the off-line reactor does not raise the level of contaminants removed to a level such that the spent regenerant cannot be reused before recovery in the benzene column. While recycling of regenerant has been performed, the regenerant is not recycled in the off-line reactor during the regeneration cycle, but is used in the process cycle. That is, the regenerant is passed to either the on-line reactor, or to another reactor such as the transalkylation reactor, wherein the regenerant is part of the process.

The benefits of recycling regenerant during the regeneration cycle include a significant reduction in the benzene requirement added to the system during the process. There are significant reductions in energy consumption as the amount of benzene needed to be process though the benzene column is reduced, and the process is integrated with the transalkylation reactor to further reduce benzene and energy requirements.

Figure 2:
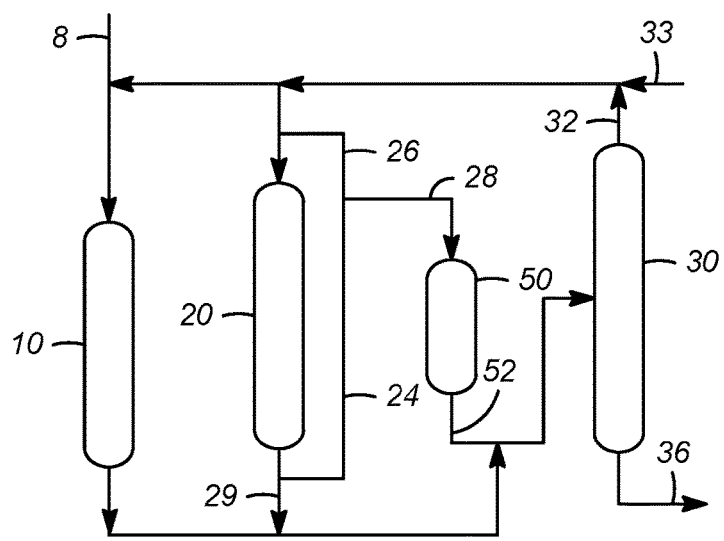
FIG. 2 is a diagram of the process flow for regeneration of an alkylation reactor.

The present invention is a process for the regeneration of an alkylation reactor, as shown in FIG. 2. The process includes taking an alkylation reactor off-line, through either stopping or substantially reducing the flow of feed 8 to the reactor to create an off-line reactor 20. A regenerant stream 32 is passed to the inlet port of the off-line reactor 20 to generate a regenerant effluent 24, during a regeneration cycle. The process further includes passing a portion 26 of the regenerant to the inlet port of the off-line reactor, wherein the portion is greater than 10 vol %. In one embodiment, the portion 26 is between 20 vol % and 99 vol %. In a preferred embodiment, the portion is between 50 vol % and 95 vol %. In a more preferred embodiment, the portion is between 70 vol % and 90 vol %, and in a most preferred embodiment, the portion is between 75 vol % and 85 vol %.

In one embodiment, the regeneration process includes a mass flux through the off-line reactor between kg/hr/m$^2$ and 500 kg/hr/m$^2$, and a preferred mass flux through the off-line reactor between 250 kg/hr/m$^2$ and 400 kg/hr/m$^2$.

The process can include purging the off-line reactor, wherein the purge is performed with the regenerant stream. The regeneration process includes passing a hot regenerant stream to the off-line reactor, or heating the reactor or regenerant stream to a regeneration temperature. The regeneration temperature is between 200° C. and 300° C. The regeneration cycle can last between 1 hour and 72 hours, with a preferred regeneration time between 10 hours and 28 hours. A typical regeneration cycle time is 24 hours.

Following the regeneration of the off-line reactor, the off-line reactor is cooled to the process temperature, and placed on-line.

The process further includes passing a second portion 28 of the regenerant effluent stream 24 to a transalkylation unit 50. The second portion 28 can be between 1 vol % and 90 vol % of the regenerant effluent stream 24, and is preferably less than 50 vol % of the regenerant effluent stream. When there is no transalkylation reactor in the process, a second portion 29 of the regenerant stream 24 is passed to the benzene column 30. The second portion 29 can be between 1 vol % and 90 vol % of the regenerant effluent stream 24, and is preferably less than 50 vol % of the regenerant effluent stream.

While the invention has been described with what are presently considered the preferred embodiments, it is to be understood that the invention is not limited to the disclosed embodiments, but it is intended to cover various modifications and equivalent arrangements included within the scope of the appended claims.

The invention claimed is:

1. A process for the regeneration of an alkylation reactor, comprising:
    taking an alkylation reactor unit off-line to create an off-line reactor, wherein the alkylation reactor unit comprises an alkylation catalyst and is operated to produce linear alkylbenzene by the alkylation of benzene with olefins;
    passing a regenerant stream comprising an aromatic to an inlet port of the off-line reactor to regenerate the alkylation catalyst and generate a regenerant effluent, during a regeneration cycle; and
    recycling a portion of the regenerant effluent directly to the inlet port of the off-line reactor, wherein the portion is greater than 10 vol % of the regenerant effluent.

2. The process of claim 1 wherein the portion is between 50 vol % and 95 vol % of the regenerant effluent.

3. The process of claim 2 wherein the portion is between 75 vol % and 85 vol % of the regenerant effluent.

4. The process of claim 1 wherein a mass flux through the off-line reactor is between 40 kg/hr/m$^2$ and 500 kg/hr/m$^2$.

5. The process of claim 4 wherein the mass flux through the off-line reactor is between 250 kg/hr/m$^2$ and 400 kg/hr/m$^2$.

6. The process of claim 1 wherein the off-line reactor is purged with the regenerant stream.

7. The process of claim 6 wherein, after being purged with the regenerant, the off-line reactor is heated to a regeneration temperature to regenerate the alkylation catalyst and generate the regenerant effluent.

8. The process of claim 7 wherein the regeneration temperature is between 200° C. and 300° C.

9. The process of claim 7 wherein, after regenerating the alkylation catalyst and generating the regenerant effluent, the off-line reactor is cooled to a process temperature.

10. The process of claim 9 wherein, after being cooled to the process temperature, the off-line reactor is placed on-line for a process cycle.

11. The process of claim 1 further comprising passing a second portion of the regenerant effluent stream to a transalkylation reaction unit.

12. The process of claim 11 wherein the second portion is less than 50 vol % of the regenerant effluent stream.

13. The process of claim 1 wherein the regenerant is benzene.

14. The process of claim 1 wherein the regeneration cycle is between 1 and 72 hours.

15. A process for the production of linear alkylbenzenes:
    passing a feedstream comprising unbranched and lightly branched olefins to an on-stream alkylation reaction unit comprising an alkylation catalyst;
    passing an aromatic stream comprising benzene to the on-stream alkylation reaction unit to react with the olefins in the feedstream to generate an effluent stream comprising linear alkylbenzenes;
    after a process cycle, taking the on-stream alkylation reaction unit off-line to create an off-stream alkylation reaction unit;
    passing a regenerant stream comprising an aromatic to the off-stream alkylation reaction unit during a regeneration cycle, thereby regenerating the alkylation catalyst and generating a regenerant effluent stream; and
    recycling a portion of the regenerant effluent stream directly to the off-stream alkylation reaction unit, wherein the portion of the regenerant effluent stream is greater than 20% of the regenerant effluent stream.

16. The process of claim 15 wherein the portion is between 75 vol % and 85 vol % of the regenerant effluent stream.

17. The process of claim 16 wherein the mass flux through the off-line reactor is between 250 kg/hr/m$^2$ and 400 kg/hr/m$^2$.

18. The process of claim 15 wherein the feedstream comprises unbranched and lightly branched olefins having from 8 to 16 carbon atoms.

19. The process of claim 15 wherein the regeneration cycle is between 1 and 72 hours.

20. The process of claim 15 further comprising passing a second portion of the regenerant effluent stream to a transalkylation reaction unit.

* * * * *